United States Patent
Martin

(10) Patent No.: US 7,661,345 B2
(45) Date of Patent: Feb. 16, 2010

(54) DEVICE FOR CLAMPING AND SEPARATING TUBING

(75) Inventor: Carl Martin, Millersburg, PA (US)

(73) Assignee: Advanced Scientifics, Inc., Millersburg, PA (US)

( * ) Notice: Subject to any disclaimer, the term of this patent is extended or adjusted under 35 U.S.C. 154(b) by 203 days.

(21) Appl. No.: 11/561,202

(22) Filed: Nov. 17, 2006

(65) Prior Publication Data
US 2008/0116241 A1   May 22, 2008

(51) Int. Cl.
*B26D 7/02* (2006.01)
*B23K 37/04* (2006.01)

(52) U.S. Cl. .............................. 83/451; 83/453; 225/96; 228/44.5

(58) Field of Classification Search .................. 83/451, 83/452, 453, 464, 468.5; 24/72.5, 455; 269/298, 269/43, 239; 225/96; 219/159, 59.1; 228/44.5, 228/49.3, 159, 158, 4.1, 44.3, 44.4
See application file for complete search history.

(56) References Cited

U.S. PATENT DOCUMENTS

| | | | | |
|---|---|---|---|---|
| 4,096,726 A | * | 6/1978 | Uhlmann et al. ............... | 72/291 |
| 4,750,662 A | * | 6/1988 | Kagimoto ................... | 228/44.5 |
| 5,090,608 A | * | 2/1992 | Jones ......................... | 228/49.3 |
| 5,330,431 A | * | 7/1994 | Herskowitz .................. | 604/153 |
| 6,646,219 B2 | * | 11/2003 | Kane et al. ................. | 219/60 A |

* cited by examiner

*Primary Examiner*—Ghassem Alie
(74) *Attorney, Agent, or Firm*—Philip D. Freedman PC

(57) ABSTRACT

A device (10) for clamping and separating a length of tubing. The device (10) comprises first and second subassemblies (12,14) for, in their closed positions, clamping the tubing at first and second locations, respectively, and at least weakening the tubing for subsequent separation. The subassemblies (12,14) face each other and are connected by a breakable connection. Each subassembly (12,14) includes clamping elements (26,34) for clamping the tubing, a perforating or cutting element (28) for perforating or otherwise weakening or cutting the tubing, and locking elements (24,32) for locking the subassembly (12,14) in the closed position. The perforating element (28) may be at least one hard plastic or metal spike. Once each subassembly (12,14) is locked in the closed position, the breakable connection is broken to result in respective lengths of clamped tubing.

20 Claims, 6 Drawing Sheets

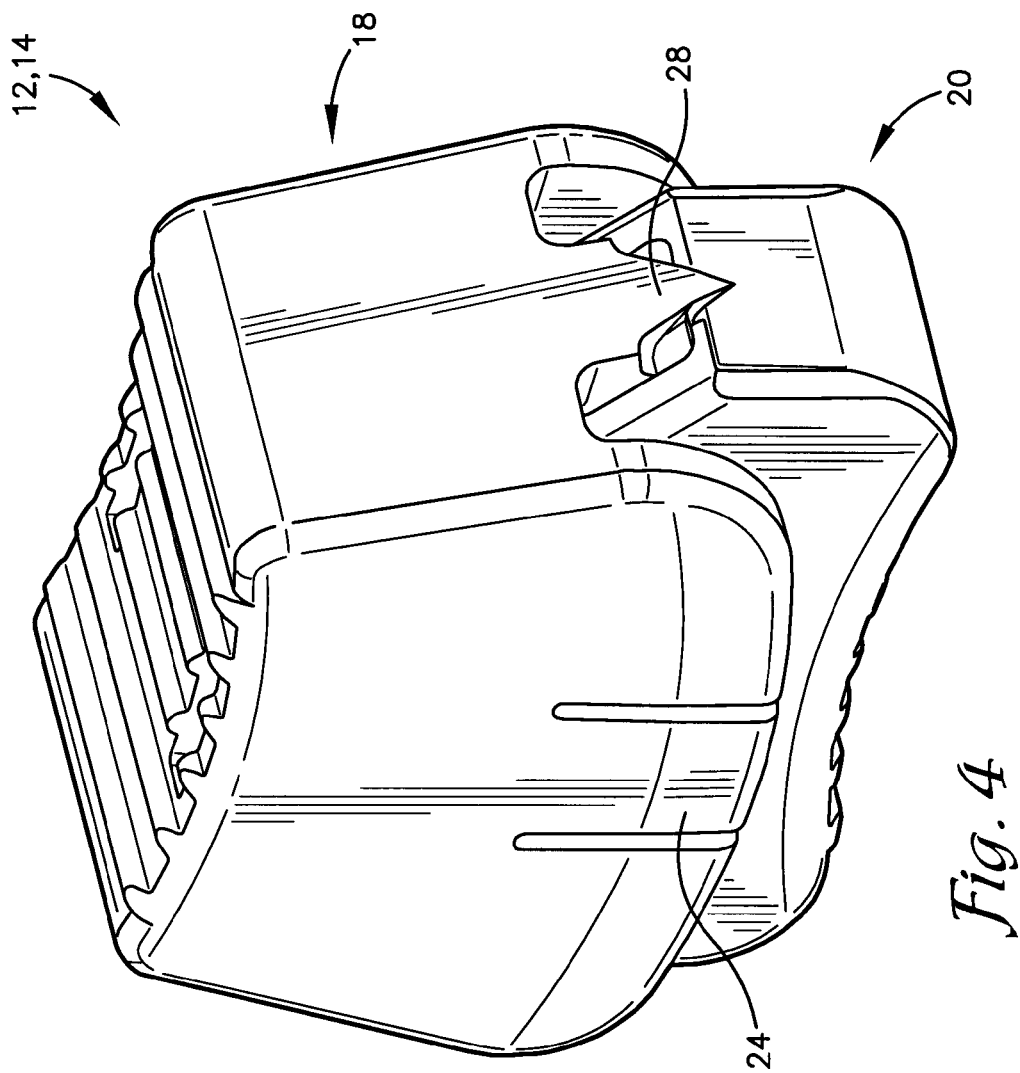

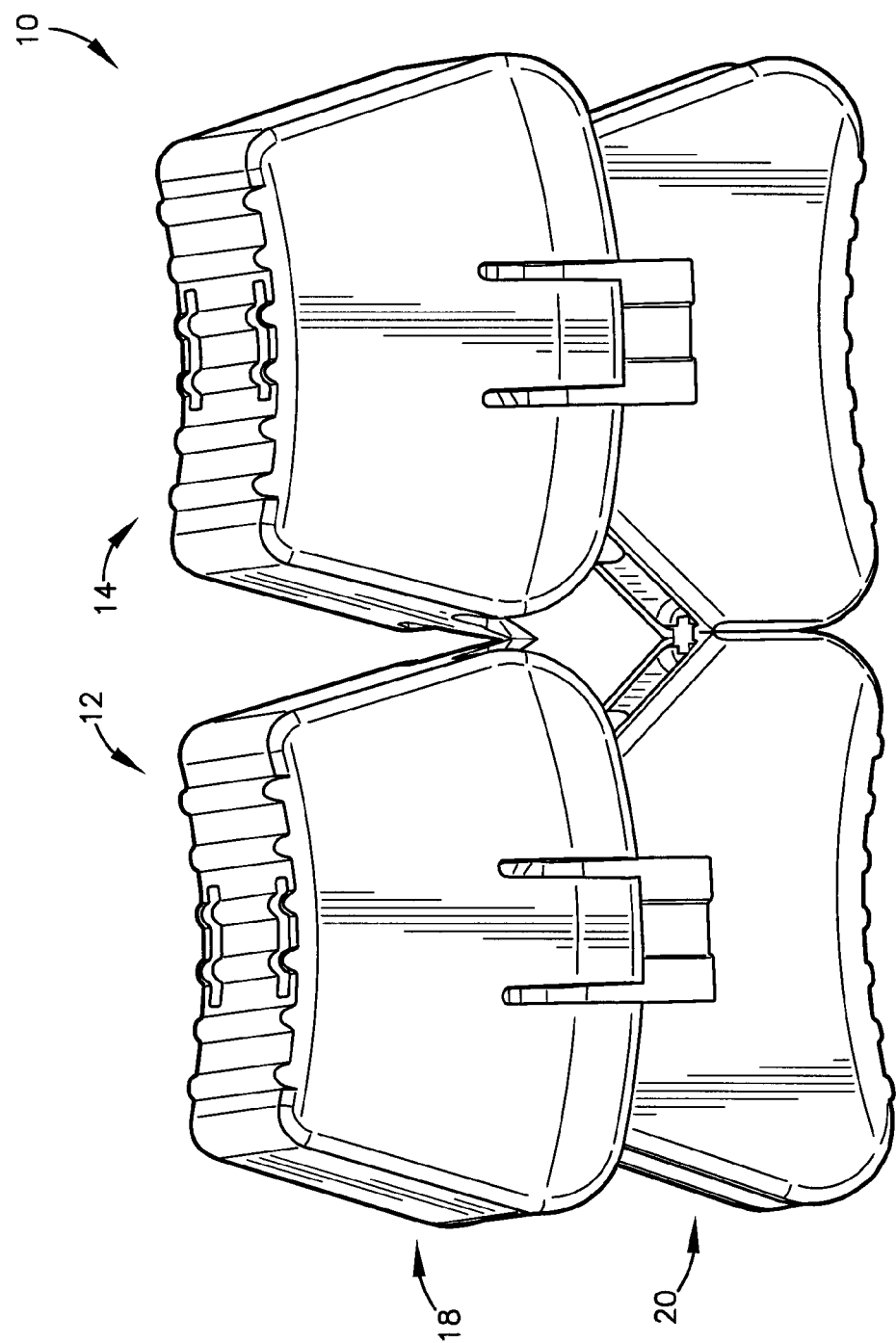

DEVICE FOR CLAMPING AND SEPARATING TUBING

FIELD OF THE INVENTION

The present invention relates to devices and techniques for clamping or otherwise sealing and separating tubing. More specifically, the present invention concerns a device having first and second subassemblies, with each subassembly being adapted and operable to substantially simultaneously perforate or otherwise weaken or cut a length of tubing and clamp the tubing on a respective side of the perforation, so that, once both subassemblies have been actuated, the subassemblies and the tubing can be separated to provide respective lengths of clamped tubing.

DESCRIPTION OF THE PRIOR ART

Tubing is often used to provide a conduit from one sterile or otherwise controlled environment to another. Various devices and techniques are known for severing this connection between the environments without sacrificing the sterility or controlled conditions. It is known, for example, to clamp such tubing at a first point using a first metal or plastic clamp, clamp it at an adjacent second point using a second clamp, and then sever the tubing between the first and second clamps. Depending on the nature and operation of the clamps, a pair of crimping pliers or other tool may be necessary to properly apply them. Similarly, a knife, scissors, or other cutting tool may be needed to sever the clamped tubing. It will be appreciated that these prior art devices and techniques are both inconvenient in that they require multiple steps, undesirable in that they require multiple tools, and prone to mistakes, such as improper application of one or both clamps, which could contaminate one or both environments.

SUMMARY OF THE INVENTION

The present invention advantageously overcomes the above-discussed and other problems with the prior art by providing a device that allows for quickly, easily, and reliably clamping and separating a length of tubing, such as a length of tubing extending between and connecting two sterile or otherwise controlled environments.

In one embodiment, the device comprises a first subassembly for, in a closed position, substantially simultaneously clamping the tubing at a first location and at least weakening the tubing for subsequent separation, and a second subassembly for, in a closed position, similarly substantially simultaneously clamping the tubing at a second location and at least weakening the tubing for subsequent separation. The first subassembly faces the second subassembly and is connected thereto by a breakable connection. Each subassembly may be independently operable. Each subassembly may include first and second clamping elements which, in the closed position, cooperate to clamp the tubing therebetween. Each subassembly may include at least one spike which, in the closed position, perforates the tubing. The spike may be constructed of hard plastic or metal. Alternatively, each subassembly may include at least one cutting element which, in the closed position, completely severs the tubing. Each subassembly may include first and second locking elements which cooperate to lock the subassembly in the closed position.

These and other features of the present invention are described in greater detail in the section titled DETAILED DESCRIPTION OF THE INVENTION, below.

BRIEF DESCRIPTION OF THE DRAWING FIGURES

A preferred embodiment of the present invention is described in detail below with reference to the attached drawings figures, wherein:

FIG. 4 is a perspective view of a subassembly of the device of FIG. 1, wherein the subassembly is shown in a closed position;

FIG. 5 is a perspective view of the device of the FIG. 1, wherein the device is shown in the open position.

DETAILED DESCRIPTION OF INVENTION

With reference to the figures, a clamping and separating device 10 is herein described, shown, and otherwise disclosed in accordance with a preferred embodiment of the present invention. Broadly, the device 10 advantageously allows for quickly, easily, and reliably clamping and separating a length of tubing, such as a length of plastic, rubber, or other flexible tubing extending between and connecting two sterile or otherwise controlled environments.

Figure 1:
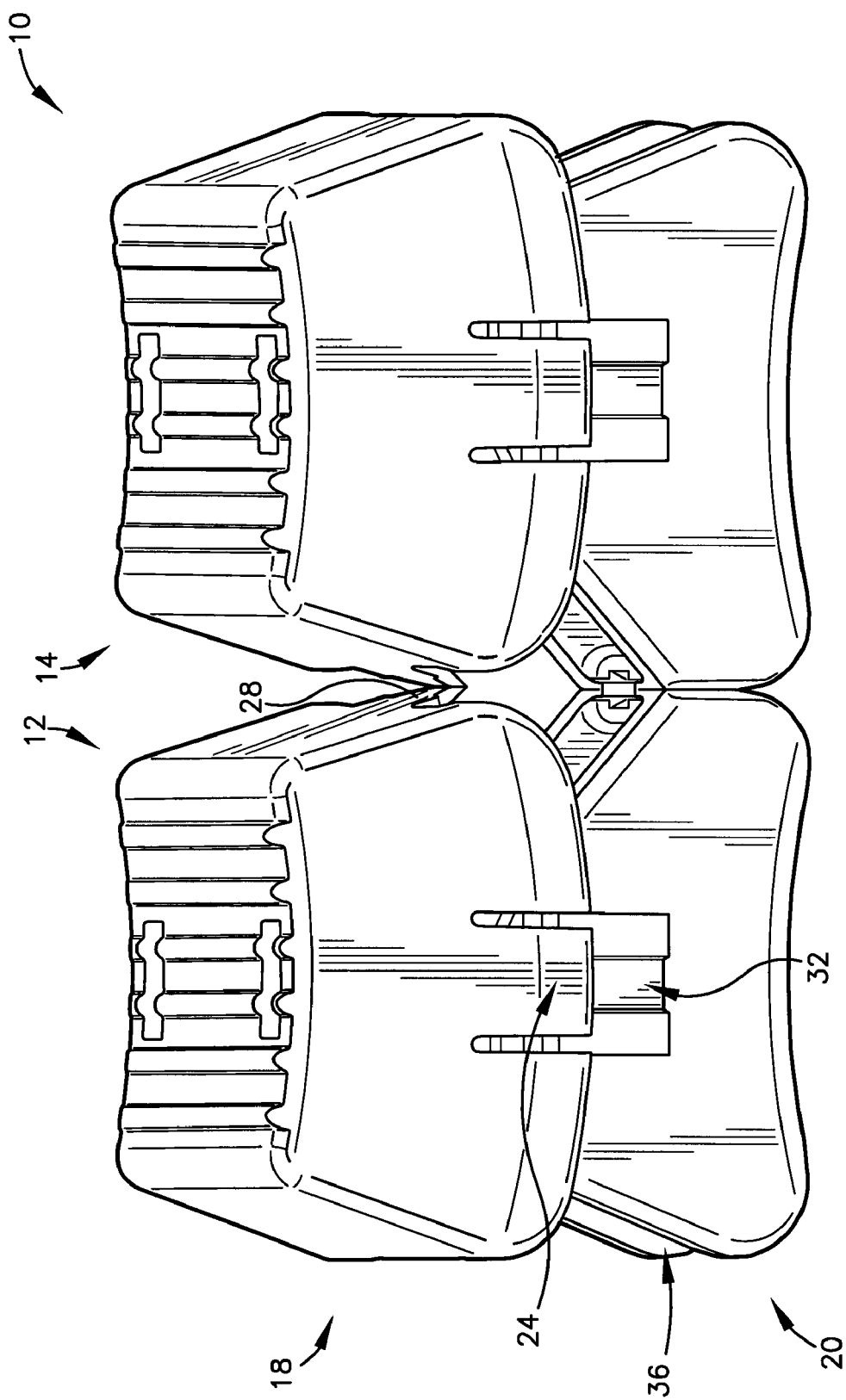
FIG. 1 is a perspective view of an embodiment of the clamping and separating device of the present invention, wherein the device is shown in an open position.
Figure 2:
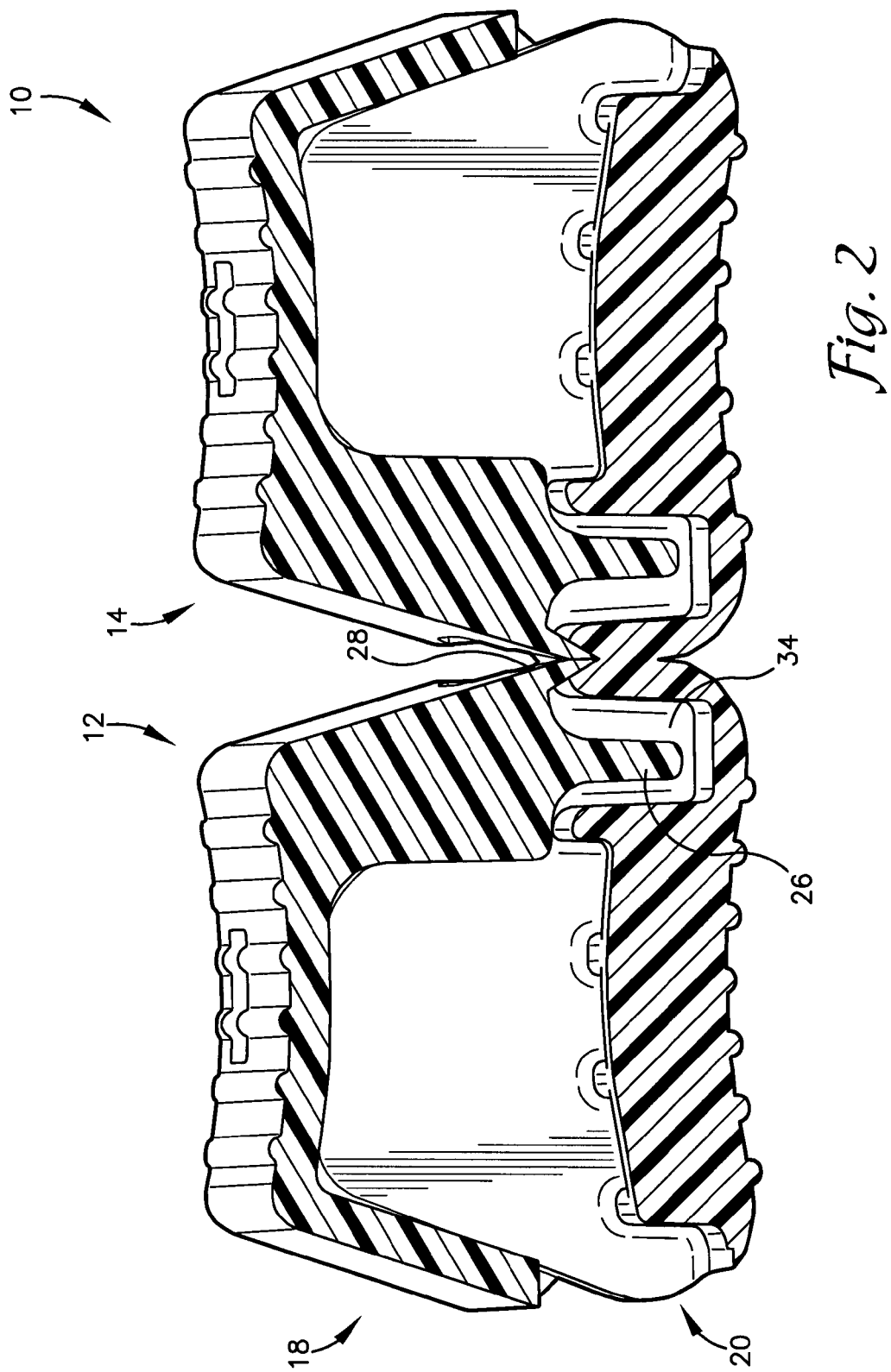
FIG. 2 is a sectional perspective view of the device of FIG. 1, wherein the device is shown in the closed position.

Referring particularly to FIGS. 1, 2, and 4 in one embodiment the device 10 comprises substantially identical first and second subassemblies 12,14. The subassemblies 12,14 are initially physically connected to one another, with the first subassembly 12 being maintained in close proximity to and facing the second subassembly 14. The connection between the subassemblies 12,14 is relatively easily breakable so as to allow for separating the subassemblies 12,14 once the tubing has been clamped and cut. Such relatively easy breakability may be accomplished by making the connection weaker than the surrounding material so that the break occurs at the connection when twisting, pulling, or other force is applied to the subassemblies 12,14.

Each subassembly 12,14 is adapted and operable, as discussed in detail below, to substantially simultaneously perforate or otherwise weaken or cut the tubing and clamp the tubing on a respective side of the perforation. As used herein, the term "substantially simultaneously" means that there is an overlap of time during which the clamping action is occurring and during which the perforating or other weakening or cutting action is occurring, and does not imply or require that the two actions begin or end at the same moment or take the same amount of time to complete. Thus, in one embodiment, for example, the clamping action begins first and the perforating or other weakening or cutting action occurs as the clamping action is being completed, thereby ensuring that the integrities of the environments connected by the tubing are maintained. Once both subassemblies 12,14 have been actuated, the subassemblies 12,14 and the tubing can be twisted, pulled apart, or otherwise easily separated to result in respective lengths of clamped tubing.

Each subassembly 12,14 includes an upper portion 18 and a lower portion 20. The upper and lower portions 18,20 are movable relative to one another between an open position (seen in FIGS. 1 and 5) in which the tubing is unclamped and uncut and a closed position (seen in FIGS. 2, 4, and 6) in which the upper and lower portions 18,20 cooperate to clamp and perforate or otherwise weaken or cut the tubing.

Each upper portion 18 includes a first locking element 24; a first clamping element 26; and a perforating element 28. Each lower portion 20 includes a second locking element 32; a second clamping element 34; and a channel 36. As shown an upper surface of the upper portion 18, and a lower surface of the lower portion 20, may be ribbed, checked, or otherwise conditioned or shaped to facilitate non-slip handling of the device 10.

Figure 3B:
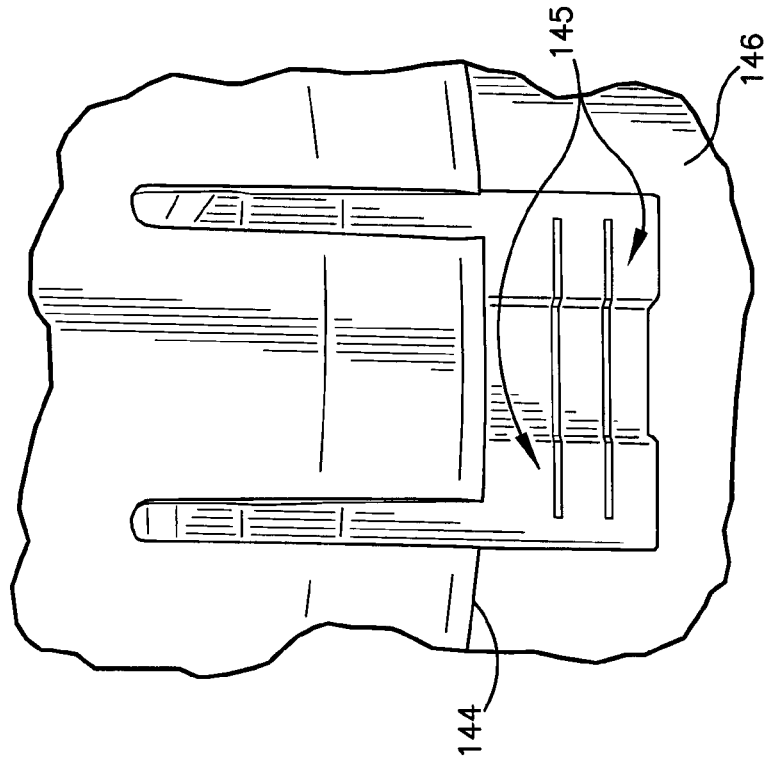
FIG. 3B is a fragmentary elevation view of a second embodiment of the locking feature.
Figure 3A:
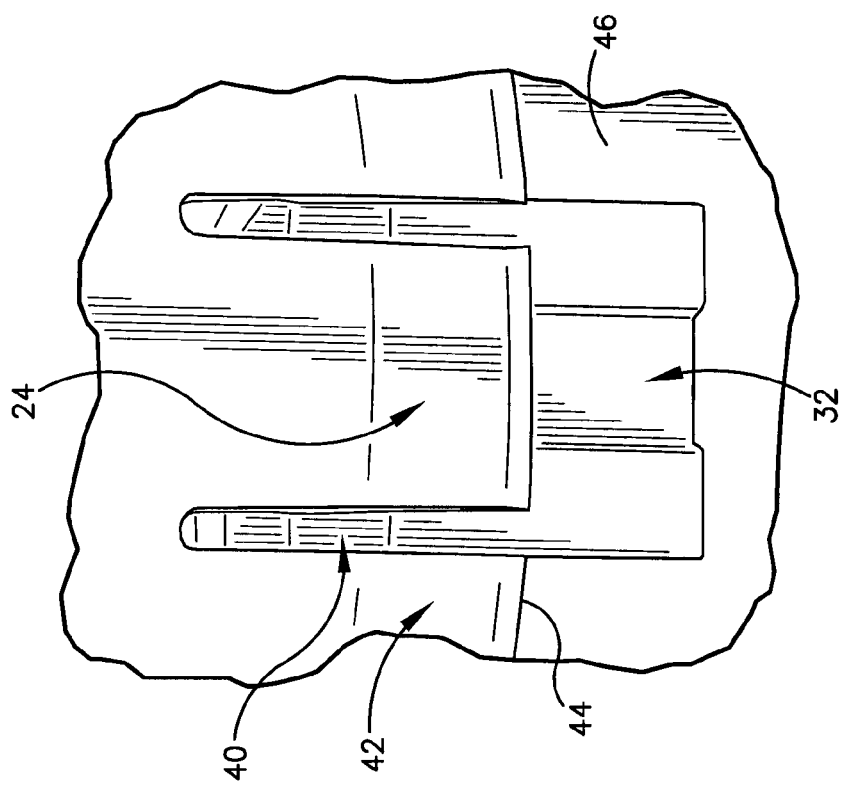
FIG. 3A is a fragmentary elevation view of a first embodiment of a locking feature of the device of FIG. 1.

The first and second locking elements 24,32 cooperate to define the open and closed positions. Referring particularly to FIG. 3A, in one embodiment the first locking element 24 includes a channel 40 and a flexible tab 42 projecting into the channel 40 and presenting a rib or tooth 44, and the second locking 32 element includes a raised surface 46. In use, the raised surface 46 slides within the channel 40 to assist in maintaining proper alignment of the upper and lower portions 18,20 as they are moved between positions. The tab 42 slides over the raised surface 46. In the closed position, the rib or tooth 44 engages an end of the raised surface 46 to lock the portions 18,20 and prevent any further relative movement therebetween, including movement back to the open position. Referring particularly to FIG. 3B, in another embodiment of the locking feature one or more grooves or recesses 145 are provided in the raised surface 146 for receiving the rib or tooth 144. Such grooves or recesses 145 may be used to define multiple clamping positions, or to provide a ratcheting effect. In yet another embodiment, the locking elements can be unlocked, or opened, after being placed into the assuming the closed position.

Referring again to FIG. 2, the first and second clamping elements 26,34 cooperate to clamp the tubing located within the channel 36. In the embodiment shown in the figures, the first clamping element 26 is a projecting member, and the second clamping element 34 is a receiver. In use, the tubing located within the channel 36 is positioned between the projecting member 26 and the receiver 34. As the upper and lower portions 18,20 are moved from the open to the closed positions, the projecting member 26 collapses the tubing and pushes it into the receiver 34, which both clamps the tubing closed and stretches, or tautens, the tubing to facilitate penetration of the tubing by the perforating element 28. In one embodiment, used on a common type of tubing, when both subassemblies 12,14 are actuated, such that the tubing is clamped between the first and second clamping elements 26,34 of each subassembly 12,14, the tubing is stretched by approximately between 0.20 inches and 0.30 inches therebetween, making the normally resilient tubing more susceptible to penetration by the perforating element 28. In another embodiment, the receiver is eliminated, such that the projecting member clamps the tubing against the bottom of the channel.

The perforating element 28 at least weakens the tubing so that it can thereafter be easily twisted or pulled apart. In one embodiment, the perforating element is a hard plastic spike or tooth able to penetrate and make a corresponding hole in the tubing. In another embodiment, the spike or tooth is metal. In yet another embodiment, there are a plurality of spikes or teeth for creating a plurality of perforations in the tubing. In yet another embodiment, the perforating element is an elongated edge for severing the tubing completely, thereby requiring no subsequent twisting or pulling to complete the severance. The elongated edge may be serrated or smooth, hard plastic or metal, such as, for example, a metal razor edge.

The channel 36 closely receives and confines the tubing without clamping, i.e., obstructing flow. Closely confining the tubing facilitates proper clamping and perforating or cutting. As such, the channel 36 may be manufactured in specific sizes to accommodate tubing of specific sizes or, at least, a relatively narrow range of sizes. In another embodiment, the channel is adapted to accommodate a broader range of tubing sizes. This may be accomplished by, for example, appropriately shaping the first and second clamping elements to force smaller tubing into proper position within the channel for perforating or otherwise weakening or cutting, or by elongating the first and second clamping elements and the perforating element to act upon smaller tubing located anywhere in the channel, or by including a removable shim within the channel to allow for selectively controlling the size of the channel, or by any combination thereof.

Figure 6:
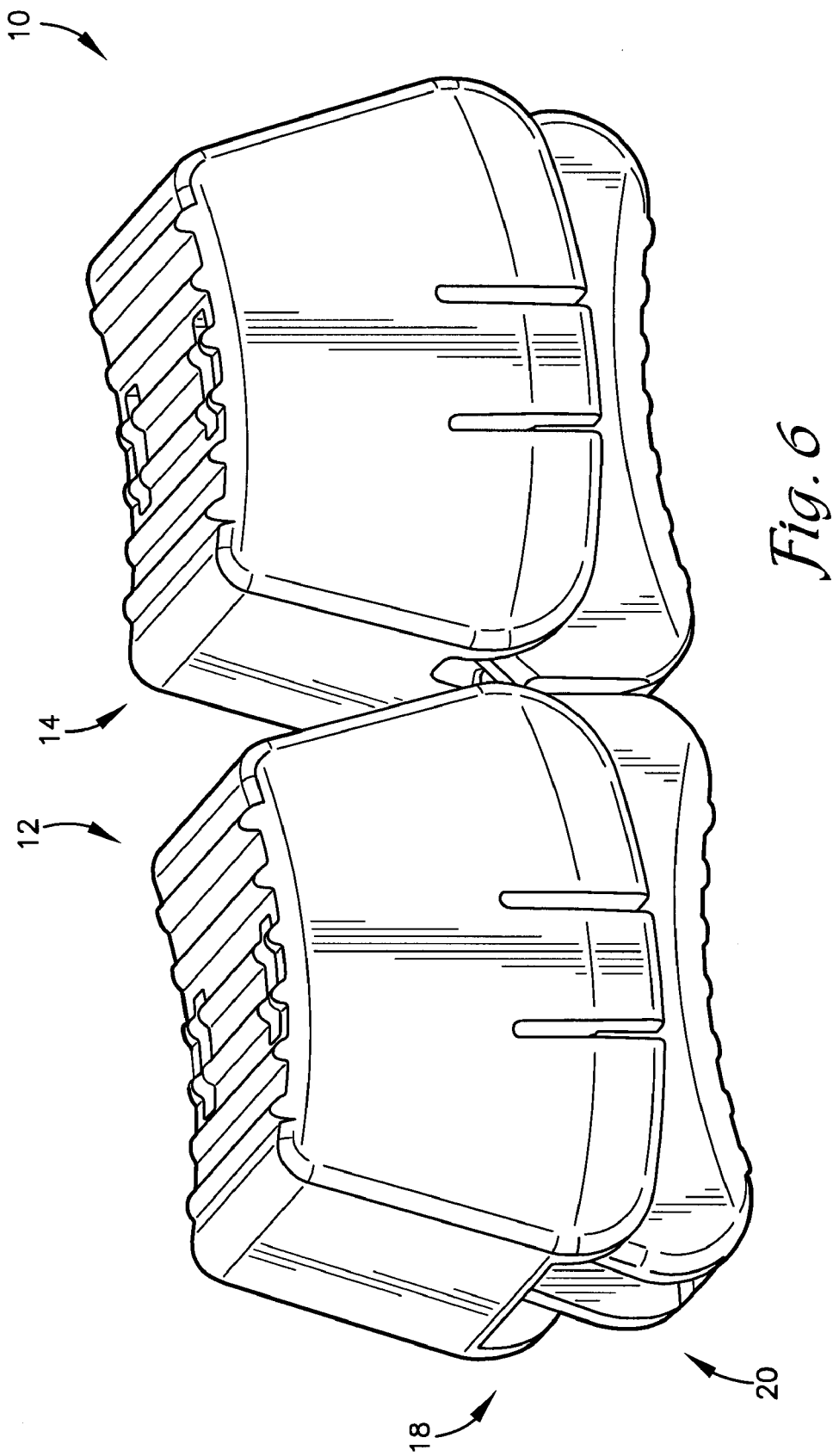
FIG. 6 is a perspective view of the device of FIG. 1, wherein the device is shown in the closed position.

In exemplary use and operation, the device 10 may be used and may function as follows. Referring particularly to FIGS. 5 and 6, given a length of tubing extending between a first sterile or otherwise controlled environment and a second sterile or otherwise controlled environment, the device 10 may be used to quickly, easily, and reliably substantially simultaneously clamp and separate the tubing as follows without contaminating either environment. First, the lower portions 20 are positioned such that the tubing is received within the channels 36. Then, the upper portions 18 are placed upon the lower portions 20 in the open position. Next, the upper portions 18 are pushed down upon the lower portions 20 toward the closed position, such that the clamping elements 26,34 clamp the tubing at first and second locations and pull it taught therebetween, the perforating elements 28 perforate the tubing at a point or points between the first and second locations, and the locking elements 24,32 engage to secure the upper and lower portions 18,20 in their closed positions. Thereafter, the subassemblies 12,14 are twisted or pulled apart to both separate the subassemblies 12,14 and finish separating the tubing, thereby resulting in two lengths of clamped tubing.

Although the invention has been described with reference to various embodiments, it is noted that equivalents may be employed and substitutions made herein without departing from the scope of the invention as recited in the claims.

Having thus described the preferred embodiment of the invention, what is claimed as new and desired to be protected by Letters Patent includes the following:

1. A device for clamping and separating tubing between sterile environments, the device comprising:
   a first subassembly for, in a closed position, substantially simultaneously clamping the tubing at a first location and at least weakening the tubing for subsequent separation; and
   a second subassembly for, in a closed position, substantially simultaneously clamping the tubing at a second location and at least weakening the tubing for subsequent separation,
   wherein the first subassembly faces the second subassembly and is connected by a breakable connection to the second subassembly to provide a continuous channel for clamped tubing within the continuous channel at a location between the first and second subassemblies so that a sterile environment is maintained on each side of the clamping elements upon separation of the breakable connection.

2. The device as set forth in claim 1, wherein each subassembly is independently operable to substantially simultaneously clamp and at least weaken the tubing.

3. The device as set forth in claim 1, wherein each subassembly includes a first clamping element and a second clamping element which, in the closed position, cooperate to clamp the tubing therebetween.

4. The device as set forth in claim 1, wherein each subassembly includes at least one spike which, in the closed position, perforates the tubing.

5. The device as set forth, in claim 4, wherein the spike is constructed of hard plastic.

6. The device as set forth in claim 4, wherein the spike is constructed of metal.

7. The device as set forth in claim 1, wherein each subassembly includes at least one cutting element which, in the closed position, completely severs the tubing.

8. The device as set forth in claim 1, wherein each subassembly further includes first and second, locking elements which cooperate to lock the subassembly in the closed position.

9. The device of claim 1 wherein
the first subassembly and second subassembly comprise a continuous channel for tubing at the breakable connection, and each subassembly includes:
a clamping element for, in a closed position, clamping the tubing at the continuous channel,
a perforating element for, in the closed position, perforating the tubing at the continuous channel between clamping elements of respective subassemblies, wherein clamping and perforating occur substantially simultaneously,
and
a locking element for locking the subassembly in the closed position.

10. The device as set forth in claim 9, wherein each subassembly is independently operable.

11. The device as set forth in claim 9, wherein the clamping element includes a projecting member positioned above the tubing, and a receiver positioned below the tubing, and wherein, in the closed position, the projecting member pushes the tubing into the receiver.

12. The device as set forth in claim 9, wherein the perforating element includes at least one spike which, in the closed position, perforates the tubing.

13. The device as set forth in claim 12, wherein the spike is constructed of hard plastic.

14. The device as set forth in claim 12, wherein the spike is constructed of metal.

15. The device of claim 1, comprising:
first and second connecting subassemblies, with the first subassembly facing the second subassembly and being connected by a breakable connection, and each subassembly including—
a clamping element including a projecting member for, in the closed position, pushing upon and collapsing the tubing,
a perforating element including at least one spike for, in the closed position, perforating the tithing between the clamping elements of the subassemblies to separate the tubing between sterile environments, wherein the clamping element and the perforating element act substantially simultaneously, and
a locking element for locking the subassembly in a closed position on respective ends of perforated and separated tubing to provide a sterile tubing closure to each of the environments.

16. The device as set forth in claim 15, wherein each subassembly is independently operable.

17. The device of claim 1, wherein at least one subassembly comprises a first locking element that includes a channel and a flexible tab projecting into the channel.

18. The device of claim 1, wherein subassembly comprises a first locking element 24 comprising a channel 40 and a second locking element comprising a flexible tab 42 that projects into the channel 40 to securely clamp the subassembly against tubing.

19. The device of claim 1, wherein subassembly comprises a first locking element 24 that comprises at least one rib or channel that fits to a raised surface 46 of the second locking element.

20. The device of claim 1 wherein a subassembly comprises a rib or tooth and another subassembly comprises at least one rib or tooth to define multiple clamping positions.

* * * * *